(12) United States Patent
Farbarik (10) Patent No.: US 7,369,757 B2
(45) Date of Patent: May 6, 2008

(54) SYSTEMS AND METHODS FOR REGULATING POWER IN A MEDICAL DEVICE

(75) Inventor: John M. Farbarik, Alameda, CA (US)

(73) Assignee: Nellcor Puritan Bennett Incorporated, Pleasanton, CA (US)

( * ) Notice: Subject to any disclaimer, the term of this patent is extended or adjusted under 35 U.S.C. 154(b) by 162 days.

(21) Appl. No.: 11/420,167

(22) Filed: May 24, 2006

(65) Prior Publication Data

US 2007/0274693 A1    Nov. 29, 2007

(51) Int. Cl.
G05F 1/10    (2006.01)
(52) U.S. Cl. .................. 388/806; 388/800; 388/803
(58) Field of Classification Search ............ 388/800, 388/803, 806
See application file for complete search history.

(56) References Cited

U.S. PATENT DOCUMENTS

| | | | | |
|---|---|---|---|---|
| 4,644,238 A | | 2/1987 | Hirosaki | 318/332 |
| 4,867,152 A | * | 9/1989 | Kou et al. | 128/204.21 |
| 5,044,362 A | * | 9/1991 | Younes | 128/204.21 |
| 5,107,830 A | * | 4/1992 | Younes | 128/204.18 |
| 5,263,369 A | * | 11/1993 | Cutler | 73/204.15 |
| 5,474,062 A | * | 12/1995 | DeVires et al. | 128/205.24 |
| 5,494,028 A | * | 2/1996 | DeVries et al. | 128/205.24 |
| 5,543,695 A | * | 8/1996 | Culp et al. | 318/432 |
| 5,690,093 A | | 11/1997 | Schrank et al. | 126/299 D |
| 5,789,829 A | | 8/1998 | Heesemann | 310/52 |
| 6,463,930 B2 | * | 10/2002 | Biondi et al. | 128/204.21 |
| 6,705,315 B2 | | 3/2004 | Sullivan et al. | 128/204.18 |
| 6,794,843 B2 | | 9/2004 | Chiang et al. | 318/781 |
| 2005/0031322 A1 | | 2/2005 | Boyle et al. | 388/800 |
| 2006/0065270 A1 | * | 3/2006 | Li | 128/204.18 |
| 2006/0213511 A1 | * | 9/2006 | Hansen | 128/200.24 |

FOREIGN PATENT DOCUMENTS

EP    1156213 B1    11/2001
WO    05016217 A2    2/2005

* cited by examiner

Primary Examiner—Rita Leykin
(74) Attorney, Agent, or Firm—Baker Botts LLP (57) ABSTRACT

A system for controlling a motor for use in a ventilation system may include a motor, a voltage adjustment system, a user interface, and a motor controller. The voltage adjustment system may be configured to adjust a voltage applied to the motor. The user interface may be configured to receive patient settings input from a user and communicate target ventilation parameters to the motor controller. The motor controller may include a calculation engine configured to calculate motor performance parameters for achieving the target ventilation parameters, and based at least on the calculated motor performance parameters, perform a voltage adjustment analysis for controlling the voltage adjustment system. The motor controller may further include a voltage adjuster controller configured to activate the voltage adjustment system based on a first result of the voltage adjustment analysis and to not activate the voltage adjustment system based on a second result of the voltage adjustment analysis.

30 Claims, 4 Drawing Sheets

SYSTEMS AND METHODS FOR REGULATING POWER IN A MEDICAL DEVICE

TECHNICAL FIELD

The present disclosure relates generally to power consumption and, more particularly, to systems and methods for regulating power in a medical device, such as a ventilator, for example.

BACKGROUND

Medical ventilators are widely utilized to provide breathing gas to a patient when the patient is unable to breath adequately without assistance. More particularly, a ventilator forces a mixture of air and oxygen into the lungs periodically to enable and assist in the vital transfer of gases into and out of the blood via the lungs when the patient is unable to breathe correctly on their own. Ventilators can employ a wide variety of breathing strategies or ventilation modes, such as pressure controlled ventilation, volume controlled ventilation, Biphase Intermittent Positive Airway Pressure (BIPAP) ventilation, and Continuous Positive Airway Pressure (CPAP) ventilation, for example.

A ventilator typically includes a power system to provide power to the various components of the ventilator. The power system may include one or more various power sources (e.g., an external DC power source, an AC power source, and/or one or more batteries), controllers, and various hardware and/or software. In some systems, the power system architecture and/or various electrical components may cause power losses in the system, which may reduce the system's efficiency and, in systems that use battery power, may reduce the battery life and/or duration of operation.

SUMMARY

In accordance with one embodiment of the present disclosure, a system for reducing power loss in a medical apparatus may include multiple power sources, a power source switch matrix, a diode, and a diode bypass switch. The power source switch matrix may control whether each power source is currently providing power to the power load. The diode may be electrically coupled to a first power source to prevent current from one or more of the other power sources from being applied to the first power source. The diode bypass switch may be coupled to the first power source and is operable to switch between a first state in which a current pathway from the first power source to the power load includes the diode and a second state providing a current pathway from the first power source to the power load that circumvents the diode.

In accordance with another embodiment of the present disclosure, a method for reducing power loss in a medical apparatus including multiple power sources, each operable to provide power to a power load of the medical apparatus, may be provided. The method may include passively and/or actively switching between the power sources to control whether each power source is currently providing power to the power load. The method may further include switching a first diode bypass switch coupled to a first one of the multiple power sources between a first state and a second state. In the first state, a current pathway from the first power source to the power load includes a first diode electrically coupled to the first power source to prevent current from one or more of the other power sources from being applied to the first power source. In the second state, a current pathway is provided from the first power source to the power load that circumvents the first diode.

In accordance with yet another embodiment of the present disclosure, a system for reducing power loss in a medical apparatus may include multiple power supply means, power source switching means, current blocking means, and bypassing means. The multiple power supply means may be capable of providing power to a power load of a medical apparatus. The power source switching means may control whether each power source is currently providing power to the power load. The current blocking means may be coupled to a first one of the power supply means for preventing current from one or more of the other power supply means from being applied to the first power supply means. The bypassing means may switch between a first state in which a current pathway from the first power supply means to the power load includes the current blocking means, and a second state providing a current pathway from the first power supply means to the power load that circumvents the first current blocking means.

In accordance with yet another embodiment of the present disclosure, a method for controlling a motor for use in a ventilation system is provided. One or more target ventilation parameters regarding the ventilation of a patient may be received. One or more motor performance parameters for achieving the one or more target ventilation parameters may be calculated. A voltage adjustment analysis for controlling a voltage adjustment system may be performed based at least on the one or more calculated motor performance parameters. The voltage adjustment system may by configured to adjust a voltage applied to the motor. The voltage adjustment system may be activated based on a first result of the voltage adjustment analysis, and not activated based on a second result of the voltage adjustment analysis. The motor may be controlled based on the one or more calculated motor performance parameters.

In accordance with yet another embodiment of the present disclosure, a method for controlling a motor for use in a ventilation system is provided. One or more target ventilation parameters regarding the ventilation of a patient may be received. A voltage adjustment analysis for controlling a voltage adjustment system may be performed based at least on the one or more received target ventilation parameters. The voltage adjustment system may be configured to adjust a voltage applied to the motor. The voltage adjustment system may be activated based on a first result of the voltage adjustment analysis, and not activated based on a second result of the voltage adjustment analysis. The motor may be controlled based on the one or more calculated motor performance parameters.

In accordance with yet another embodiment of the present disclosure, a method for controlling a motor for use in a ventilation system is provided. One or more parameters regarding the ventilation of a patient may be received. A particular motor performance level corresponding to the one or more received parameters may be identified from a plurality of motor performance levels. A voltage adjustment system may be controlled based on the identified motor performance level, which may include activating the voltage adjustment system if the identified motor performance level is a first performance level, and not activating the voltage adjustment system if the identified motor performance level is a second performance level. Activating the voltage adjustment system may adjust a voltage applied to the motor.

In accordance with yet another embodiment of the present disclosure, a system for controlling a motor for use in a ventilation system is provided. The system may include a motor, a voltage adjustment system, a user interface, and a motor controller. The voltage adjustment system may be operable to adjust a voltage applied to the motor. The user interface may be configured to receive patient settings input from a user and to communicate one or more target ventilation parameters. The motor controller may be configured to receive the one or more target ventilation parameters from the user interface. The motor controller may include a calculation engine configured to calculate one or more motor performance parameters for achieving the one or more target ventilation parameters, and based at least on the one or more calculated motor performance parameters, perform a voltage adjustment analysis for controlling the voltage adjustment system. The motor controller may further include a voltage adjuster controller configured to activate the voltage adjustment system based on a first result of the voltage adjustment analysis and to not activate the voltage adjustment system based on a second result of the voltage adjustment analysis.

In accordance with yet another embodiment of the present disclosure, a system for controlling a motor for use in a ventilation system is provided. The system may include motor means and voltage adjusting means for adjust a voltage applied to the motor means. The system may also include interface means for receiving patient settings input from a user and for communicating one or more target ventilation parameters. The system may further include motor controlling means for receiving the one or more target ventilation parameters from the interface means, calculating one or more motor performance parameters for achieving the one or more target ventilation parameters, and based at least on the one or more calculated motor performance parameters, performing a voltage adjustment analysis for controlling the voltage adjustment system. The system may further include voltage adjustment controlling means for activating the voltage adjusting means based on a first result of the voltage adjustment analysis and to not activate the voltage adjusting means based on a second result of the voltage adjustment analysis.

In accordance with yet another embodiment of the present disclosure, a computer-readable medium including computer-executable instructions for controlling a motor for use in a ventilation system is provided. The computer-executable instructions may include instructions for receiving one or more target ventilation parameters regarding the ventilation of a patient; instructions for calculating one or more motor performance parameters for achieving the one or more target ventilation parameters; instructions for performing a voltage adjustment analysis for controlling a voltage adjustment system configured to adjust a voltage applied to the motor, the voltage adjustment analysis based at least on the one or more calculated motor performance parameters; instructions for activating the voltage adjustment system based on a first result of the voltage adjustment analysis; instructions for not activating the voltage adjustment system based on a second result of the voltage adjustment analysis; and instructions for controlling the motor based on the one or more calculated motor performance parameters.

BRIEF DESCRIPTION OF THE DRAWINGS

A more complete understanding of the present embodiments may be acquired by referring to the following description taken in conjunction with the accompanying drawings, in which like reference numbers indicate like features, and wherein.

DETAILED DESCRIPTION

Embodiments are best understood by reference to FIGS. 1 through 6, wherein like numbers are used to indicate like and corresponding parts.

Figure 1:
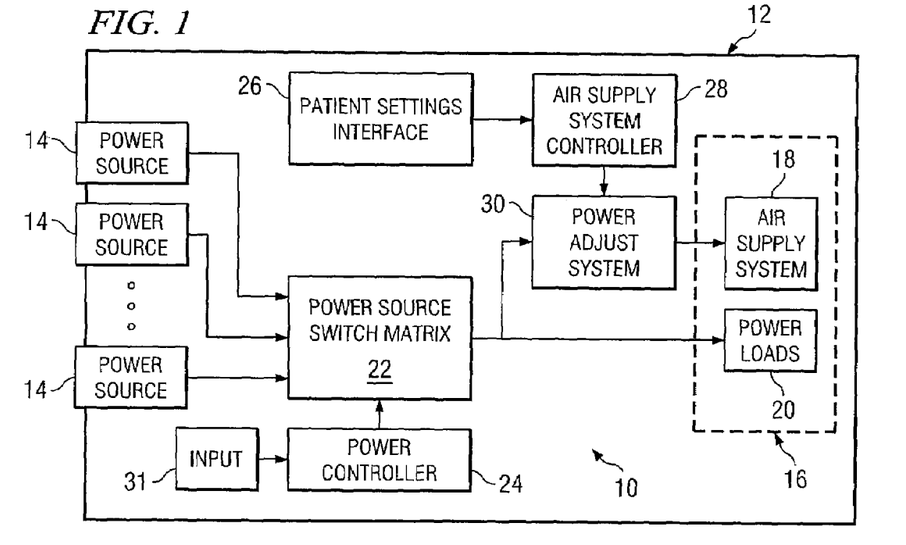
FIG. 1 is an example schematic of a power system for a medical apparatus, in accordance with one embodiment of the disclosure.

FIG. 1 is an example schematic of a power management system 10 for a medical apparatus 12 having one or more power sources 14, in accordance with one embodiment of the disclosure. For example, and not by way of limitation, medical apparatus 12 may be a ventilator or other medical apparatus having a DC power source and one or more swap batteries operable to seamlessly provide power to the medical apparatus 12, e.g., when the DC power source is removed or disconnected. Although this document focuses on ventilators and ventilation assistance, medical apparatus 12 may comprise any other suitable type of system or apparatus. In addition, as used throughout this document, the term "ventilator" may refer to any device, apparatus, or system for delivering breathing gas to a patient, e.g., a ventilator, a respirator, a CPAP device, or a BiPAP device. The term "patient" may refer to any person who is receiving support (e.g., breathing support) from medical apparatus 12, regardless of the medical status, official patient status, physical location, or any other characteristic of the person. Thus, for example, patients may include persons under official medical care (e.g., hospital patients), persons not under official medical care, persons receiving care at a medical care facility, persons receiving home care, etc.

Medical apparatus 12 may include power management system 10 and one or more power loads 16. Power loads 16 may include any component of medical apparatus 12 that may use power for its operation. For example, in the embodiment shown in FIG. 1, power loads 16 may include an air supply system 18 and one or more other power loads 20. Air supply system 18 may include any device or devices operable to generate and/or supply pressurized gas (e.g., pressurized air and/or pressurized $O_2$) for delivery to a patient, e.g., via a patient circuit. For example, air supply system 18 may include one or more blower motors operable to output compressed gas, one or more piston-based air compressors operable to output compressed gas, tanks or other containers of pre-compressed gas, any combination thereof, or any other suitable device or devices operable to generate and/or supply pressurized gas. Other power loads 20 may include any other component(s) of medical apparatus 12 that may use power for their operation, e.g., a graphical user interface (GUI), an LCD display, lighting, a cooling fan, valves, sensors and/or monitors.

Power management system 10 may be generally operable to provide and/or regulate power provided to power loads 16. Power management system 10 may include one or more power sources 14, a power source switch matrix 22, a power controller 24, a patient settings interface 26, an air supply system controller 28, and/or a power adjust system 30. Power sources 14 may include any potential source of power for a medical apparatus, such as an external AC power source, an external DC power source, and/or any suitable types of batteries, for example. In some embodiments, an external DC power source may include a DC/DC converter or an AC/DC converter. One or more power sources 14 may be removable from power management system 10. For example, a DC power source may be plugged into and/or unplugged from power management system 10. As another example, one or more batteries may be inserted into and/or removed from power management system 10. In some embodiments, power sources 14 may include one or more "swappable" or "hot swappable" batteries. In a particular embodiment, discussed in detail below with reference to FIG. 2, power sources 14 may include an external DC power source and two swappable batteries.

Power source switch matrix 22 may be generally operable to control which power source 14 (or in some embodiments or instances, power sources 14) provides power to power loads 16, e.g., to air supply device 18 and/or other power loads 20. In some embodiments, power source switch matrix 22 may provide passive switching and/or active switching between power sources 14 to control whether each power source 14 is currently providing power to power loads 16. For example, as discussed in greater detail below with reference to FIG. 2, in some embodiments, multiple power sources 14 may be coupled to power loads 16 in a configuration that allows for automatic passive switching between the multiple power sources 14 such that the power source currently having the highest voltage of the multiple power sources 14 provides power to power loads 16. In addition, in some embodiments, as discussed in greater detail below with reference to FIG. 2, power source switch matrix 22 may include one or more diodes operable to control the direction of current from one or more power sources 14, and one or more diode bypass switches operable to allow the diodes to be circumvented, in order to reduce power losses caused by the diodes.

Figure 2:
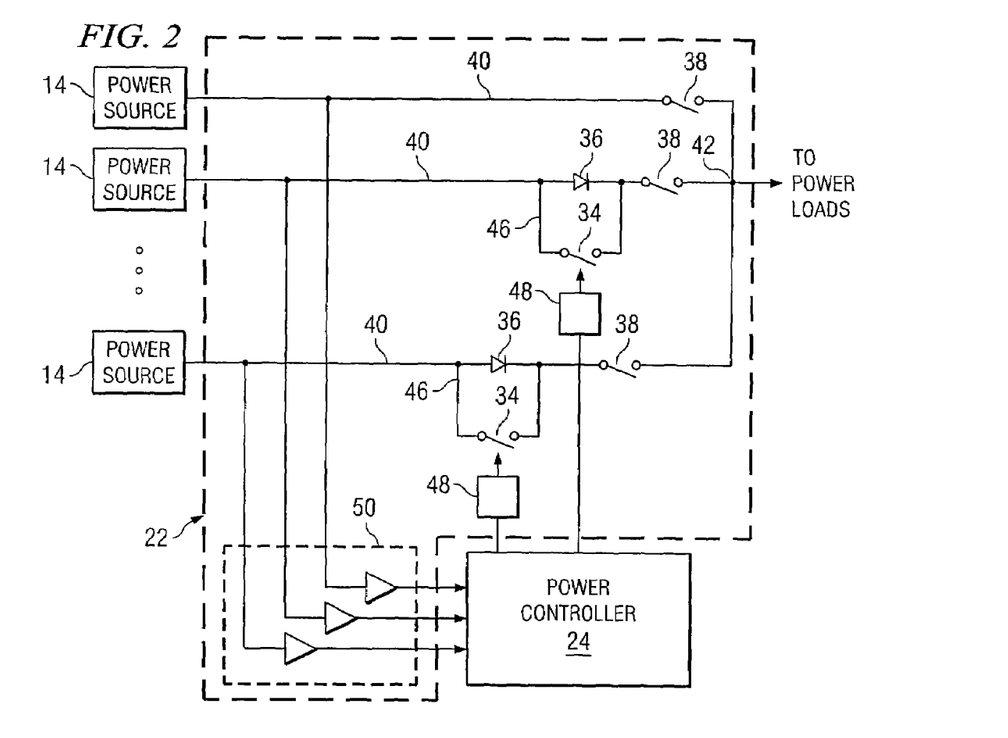
FIG. 2 is an example schematic illustrating particular features of a power source switch matrix of the power system of FIG. 1, in accordance with certain embodiments of the disclosure.

In some embodiments, power source switch matrix 22 may also include active switching between multiple power sources 14, which switching may be configured to cooperate with and/or override certain passive switching provided by power source switch matrix 22. Active switching provided by power source switch matrix 22 may be controlled by power controller 24, which may generally be operable to control switching between power sources 14 providing power to power loads 16 based on various input 31 and/or otherwise control power being supplied to power loads 16. Input 31 may include various types of information and/or feedback communicated to power controller 24, such as input from one or more user interfaces (e.g., on/off switches, a GUI, and/or other user-activated controls) and/or input from various sensors and/or monitors (e.g., sensors and/or monitors detecting voltages, currents, and/or various air flow characteristics, such as $O_2$ concentration, air flow volume, air pressure, and/or air temperature).

Power controller 24 may include any one or more types of processors, such as a microcontroller, a digital signal processor (DSP), or a field-programmable gate array (FPGA), for example. In some embodiments, power controller 24 may include software or executable code for analyzing input 31 to control switching between power sources 14 and/or otherwise control power being supplied to power loads 16. Such software may include any suitable algorithms, logic, or instructions for processing input 31, and may be stored in any suitable data storage media. In embodiments in which power controller 24 includes an FPGA, all or portions of the functionality of such software may instead be programmed into the FPGA rather than provided as separate software.

Patient settings interface 26 may include any one or more user interfaces allowing a user to access, set, modify, or otherwise control one or more settings related to the ventilation assistance provided by medical apparatus 12.

An air supply system controller 28 may control the operation of air supply system 18. For example, in an embodiment in which air supply system 18 comprises a blower motor, controller 28 may control the operation (e.g., the rotational speed, acceleration, and/or rotor position) of the motor. In addition, controller 28 may control the operation of power adjust system 30 to adjust the voltage (and thus, the power) provided to one or more power loads 16 (e.g., air supply system 18). For example, in some embodiments, power adjust system 30 may be operable to "boost," or increase, the voltage provided to one or more power loads 16 (e.g., air supply system 18). In other embodiments, power adjust system 30 may be operable to decrease the voltage provided to one or more power loads 16. In other embodiments, power adjust system 30 may be operable to both increase ("boost") and decrease the voltage provided to one or more power loads 16 as appropriate.

As discussed above, power adjust system 30 may be operable to "boost," or increase, the voltage provided to one or more power loads 16. For example, in the embodiment shown in FIG. 1, power adjust system 24 may be operable to "boost" the power provided to air supply system 18 as appropriate, based on particular operating parameters. For example, power adjust system 24 may "boost" the voltage provided to air supply system 18 for high performance operation, such as when operating at high altitudes or for providing air to a large patient, for instance. In other embodiments, power adjust system 30 (or another power adjust system) may "boost" the voltage supplied to one or more other power loads 20.

Similarly, in some embodiments, power adjust system 30 may be operable to actively decrease the voltage provided to one or more power loads 16. For example, power adjust system 24 may be operable to actively decrease the voltage provided to air supply system 18 as appropriate, based on particular operating parameters. For example, power adjust system 24 may decrease the voltage provided to air supply system 18 for low performance operations.

Patient settings interface 26, air supply system controller 28, and power adjust system 30 are discussed in greater detail below with reference to FIGS. 4-6.

FIG. 2 is an example schematic illustrating particular features of power source switch matrix 22 of power management system 10, in accordance with certain embodiments of the disclosure. Depending on the particular embodiment, power source switch matrix 22 shown in FIG. 2 may provide (a) automatic and passive switching between multiple power sources 14 such that the power source 14 currently having the highest voltage of the multiple power sources 14 provides power to power management system 10, (b) active switching between power sources 14, or active control of whether each power source 14 is available for providing power to power management system 10, and/or (c) active control one or more diode bypass switches 34 to activate/deactivate current pathways circumventing one or more diodes 36, in order to reduce power losses caused by diodes 36.

Automatic and passive switching between multiple power sources 14 may be provided based on the configuration in which power sources 14 are connected to each other and to power loads 16, e.g., as shown in FIG. 2. Active switching between multiple power sources 14 may be provided in any suitable manner. For example, as shown in FIG. 2, the current pathway 40 associated with each power source 14 (or in other embodiments, particular power sources 14) may include a circuit connect switch 38 that may be switched between a first state in which the relevant power source 14 is connected to the circuit such that the power source 14 is capable of providing power to the power loads 16 and a second state in which the power source 14 is disconnected from the circuit such that the power source 14 is incapable of providing power to the power loads 16. In some embodiments, power controller 24 is configured to actively control each circuit connect switch 38 based on various input, e.g., input 31.

Power controller 24 may switch a particular circuit connect switch 38 to disconnect a particular power source 14 from the circuit for various reasons. For example, power controller 24 may disconnect a DC power source identified as being unstable or volatile. As another example, power controller 24 may disconnect a particular power source to avoid a current rush, which may damage components or circuitry or undesirably trigger protection circuitry (e.g., blowing a fuse).

It should be understood that power source switch matrix 22 may include any one or more other components and/or provide any other suitable functionality not expressly shown in FIG. 2.

In the example embodiment shown in FIG. 2, power source switch matrix 22 includes multiple power sources 14 connected in parallel such that current pathways 40 associated with each power source 14 meet at a common node 42 leading to power loads 16. The current pathways 40 associated with each power source 14 may or may not include a diode 36 configured to prevent current from the other power sources 14 from being applied to that power source 14. For example, in certain embodiments in which power sources 14 include an external DC power source and one or more batteries, the current pathway 40 associated with each battery may include a diode 36 to prevent current from the external DC power source and/or other batteries (if present) from being applied to that battery when that battery is not currently providing power to power management system 10. In some embodiments, the current pathway 40 associated with each power source includes a diode 36.

Each current pathway 40 having a diode 36 may include a diode bypass switch 34 operable to provide a pathway circumventing diode 36. In particular, a diode bypass switch 34 may be switched between a deactivated, or open, state in which current running from the relevant power source 14 to node 42 must run through the diode 36 on that current pathway 40, and an activated, or closed, state providing a bypass circuit 46 allowing current to circumvent the diode 36. In other words, when diode bypass switch 34 is deactivated (i.e., open), current must run through diode 36, which converts a portion of the power to waste heat, whereas when diode bypass switch 34 is activated (i.e., closed), thus completing the bypass circuit 46, current may bypass diode 36, thus reducing or eliminating power losses caused by diode 36. Diode bypass switches 34 may comprise any suitable switches that may be actively controlled. For example, diode bypass switches 34 may comprise transistors, such as p-channel or n-channel MOSFET transistors, for instance.

Each diode bypass switch 34 may be actively controlled (i.e., activated/deactivated) by power controller 24 based on any suitable input, e.g., input 31 received by power controller 24. In embodiments in which diode bypass switches 34 comprise MOSFET transistors, power controller 24 may communicate signals to a gate drive 48 to activate/deactivate each diode bypass switch 34. In some embodiments, power controller 24 may maintain a diode bypass switch 34 corresponding to a particular power source 14 in the deactivated (i.e., open) state when another power source 14 is providing power to power management system 10, may activate (i.e., close) diode bypass switch 34 when (or sometime after) the particular power source 14 switches to providing power to power management system 10, and may deactivate (i.e., open) diode bypass switch 34 when (or sometime after) another power source 14 switches to providing power to power management system 10.

In this embodiment, input 31 may include, e.g., signals received from voltage monitoring devices 50 coupled to, and operable to monitor the voltage of, each power source 14. In one embodiment, each voltage monitoring device 50 may be operable to detect when the voltage of the respective power source 14 falls below and/or rises above a particular threshold value, and notify power controller 24 of such events. In other embodiments, each voltage monitoring device 50 may continuously, periodically, or otherwise detect and communicate to power controller 24 the voltage of the respective power source 14. Based on such input 31 received from voltage monitoring devices 50, power controller 24 may determine when the power source 14 currently providing power to power management system 10 has switched, and activate or deactivate one or more diode bypass switches 34 accordingly.

For example, in an embodiment in which power sources 14 include an external DC power source and two swappable batteries, when the DC power source is connected and providing power to power management system 10, power controller 24 may maintain diode bypass switches 34 corresponding to each of the batteries in the deactivated (i.e., open) state such that the diodes 36 corresponding to each of the batteries remain in effect (in order to prevent current from the DC power source from be applied to the batteries). In some embodiments, when the DC power source is removed or disconnected from power management system 10, the system may automatically and passively switch to the battery having the highest voltage to provide power to power system 10 (or in some embodiments, to multiple batteries having the same voltage such that the multiple batteries discharge simultaneously). As a result, power controller 24 may determine, based at least on input 31 from voltage monitoring devices 50, that the DC power source was removed or disconnected and that the particular battery is now supplying power to power management system 10. In response, power controller 24 may activate (i.e., close) the diode bypass switch 34 corresponding with the particular battery such that the current provided by the particular battery may bypass the corresponding diode 36, thus reducing or eliminating power losses caused by the diode 36. Power controller 24 may maintain the diode bypass switch 34 corresponding to the other battery in the deactivated (i.e., open) state in order to protect that battery.

Figure 3:
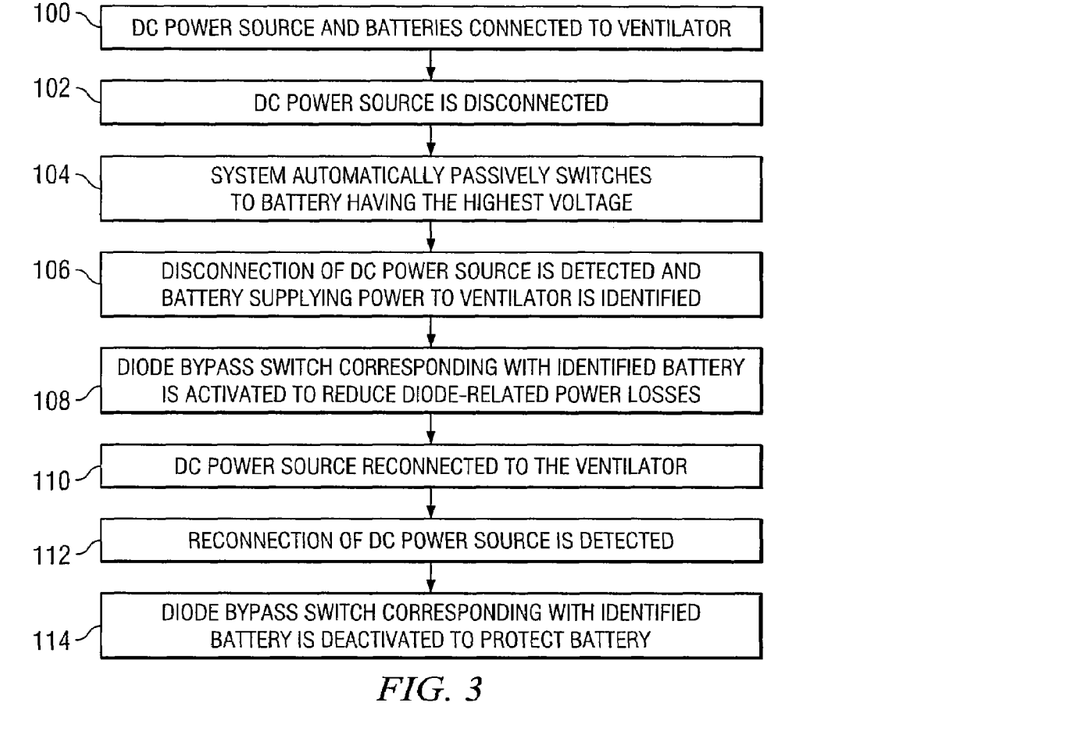
FIG. 3 illustrates a method for reducing power loss in a medical apparatus using the power system shown in FIG. 1, according to one embodiment of the disclosure.

FIG. 3 illustrates a method for reducing power loss in a medical apparatus 12 using the power system shown in FIG. 1, according to one embodiment of the disclosure. In this example embodiment, medical apparatus 12 comprises a portable ventilator including three power sources 14, namely, an external DC power source and two swappable batteries, each of which power sources 14 may be connected to and/or disconnected from medical apparatus 12 as desired. Generally, when the DC power source is connected (i.e., plugged in), the DC power source provides power to the power loads 16 of medical apparatus 12, and when the DC power source is disconnected (i.e., unplugged), one of the two swappable batteries seamlessly takes over to provide power to medical apparatus 12.

At step 100, the DC power source and both batteries are connected (i.e., plugged in) to the ventilator. For example, the patient may be using the ventilator at home and the DC power source (which in this example may include an AC/DC converter) may be plugged into the wall outlet. The DC power source has a higher voltage than either of the batteries, and thus, based on the configuration of the power sources 14, provides power to the ventilator to operate air supply system 18 and/or other power loads 20. While the DC power source is providing power to the ventilator, power controller 24 may maintain diode bypass switches 34 corresponding to each of the two swappable batteries in the deactivated (i.e., open) state such that the diodes 36 corresponding to each of the two batteries remain in effect, in order to prevent current from the DC power source from be applied to the batteries, as discussed above.

At step 102, the DC power source is disconnected (i.e., unplugged) from the ventilator and/or the wall outlet, e.g., if the patient moves or is moved outside the range of the DC power cord. As another example, the DC power cord may be mistakenly and suddenly unplugged. At step 104, in response to the DC power source being disconnected, the system may automatically and passively switch to the battery having the highest voltage to provide power to the ventilator (or in some embodiments, to multiple batteries having the same voltage such that the multiple batteries discharge simultaneously). At step 106, voltage monitoring devices 50 and/or power controller 24 may determine that the DC power source was disconnected from the ventilator and/or identify the battery now supplying power to the ventilator. In response, at step 108, power controller 24 may activate (i.e., close) the diode bypass switch 34 corresponding with the identified battery such that the current provided by that battery may bypass its corresponding diode 36, thus reducing or eliminating power losses caused by that diode 36. For example, power controller 24 may communicate a signal to an appropriate gate drive 48 to activate the diode bypass switch 34. Power controller 24 may maintain the diode bypass switch 34 corresponding to the other battery in the deactivated (i.e., open) state in order to protect that battery.

At step 110, the DC power source may be reconnected to the ventilator. For example, a caretaker may plug the unplugged DC power source back into the ventilator or the wall outlet. In some embodiments, the system may actively or passively switch back to the DC power source to provide power to the ventilator, based on various factors (e.g., the presence and state of circuit control switches 38 and the voltage of the DC power source relative to that of the batteries).

At step 112, voltage monitoring devices 50 and/or power controller 24 may determine that the DC power source was reconnected to the ventilator and/or now supplying power to the ventilator. In response, at step 114, power controller 24 may deactivate (i.e., open) the diode bypass switch 34 corresponding with the battery previously providing power to the ventilator when the DC power source was reconnected, such that the diode 36 corresponding with that battery prevents current from the DC power source from reaching the battery.

As discussed above, power management system 10 may include a patient settings interface 26, air supply system controller 28, and/or power adjust system 30 to control the operation of air supply system 18, e.g., by controlling the voltage or power supplied to air supply system 18.

Figure 4:
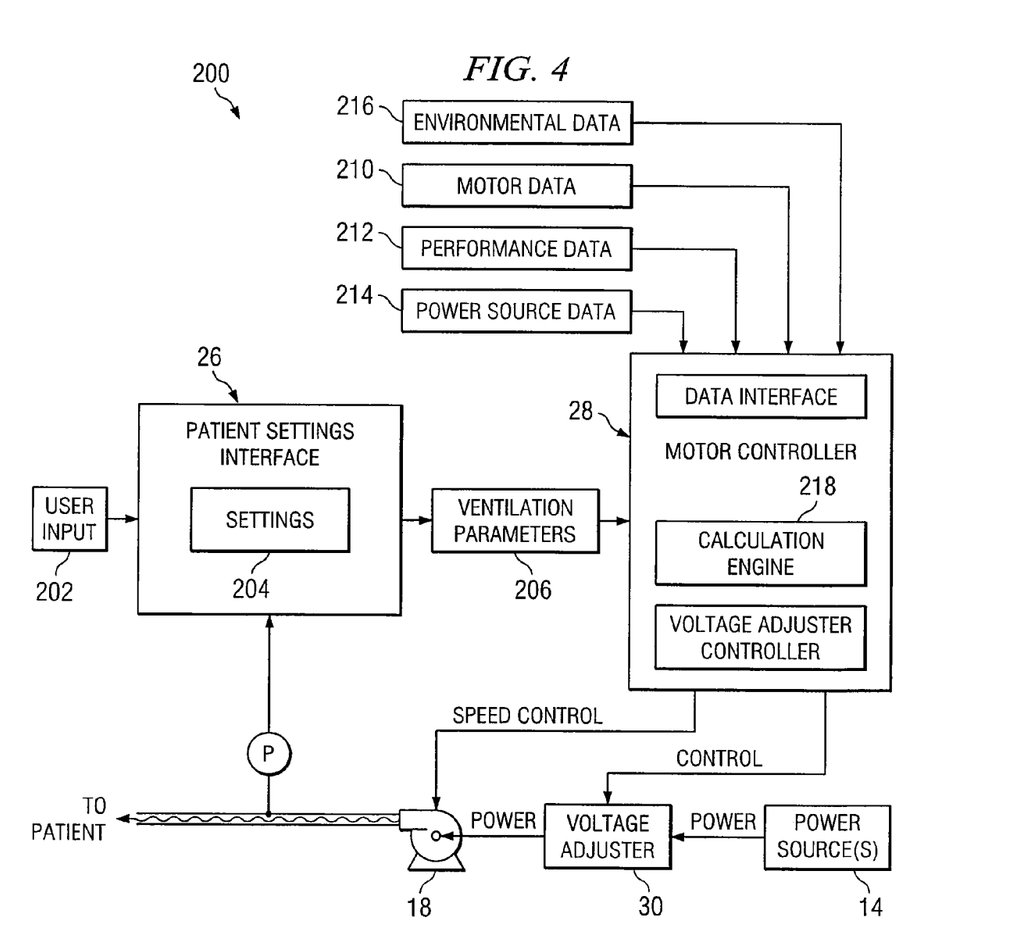
FIG. 4 is an example block diagram of a system for controlling the operation of air supply system (e.g., a blower motor), in accordance with one embodiment.

FIG. 4 is an example block diagram of a system 200 for controlling the operation of air supply system 18, in accordance with one embodiment. System 200 may include air supply system 18, patient settings interface 26, air supply system controller 28, and/or power adjust system 30. In this example embodiment, air supply system 18 comprises a blower motor, air supply system controller 28 comprises a motor controller, and power adjust system 30 comprises a voltage adjuster.

As discussed above, patient settings interface 26 may include any one or more user interfaces allowing a user to provide user input 202 to access, set, modify, or otherwise control one or more patient settings 204 related to the ventilation assistance provided by ventilator 12. Such patient settings 204 may include, e.g., patient or environmental parameters (e.g., the patient's weight, age, condition, other physiological information regarding the patient, and/or the altitude) and/or breath delivery parameters (e.g., desired pressure and/or flow volume). Patient settings interface 26 may include a graphical user interface and/or one or more manual controls. A graphical user interface may include a display device (e.g., a touch screen) configured to display various patient settings 204 and/or provide an interface for accepting input 202 from a user via the display device to access, set, modify, or otherwise control one or more patient settings 204.

Patient settings interface 26 may be configured to communicate one or more target ventilation parameters 206 to motor controller 28. Target ventilation parameters 206 may include, e.g., user input 202, patient settings 204, and/or data derived from or otherwise associated with patient settings 204 (e.g., a motor speed to provide a particular target pressure or flow volume defined by patient settings 204, or a particular motor speed reached within a particular time to provide a particular target pressure or flow volume defined by patient settings 204).

Motor controller 28 may control the operation (e.g., the rotational speed, acceleration, and/or rotor position) of blower motor 18. In some embodiments, controller 28 may control the operation of blower motor 18 by regulating the voltage and/or current delivered to blower motor 18. In addition, controller 28 may control the operation of voltage adjuster 30 to adjust (e.g., boost or decrease) the voltage (and thus, the power) provided to blower motor 18. For example, controller 28 may activate voltage adjuster 30 if the voltage supplied to motor 18 by the currently-active power source 14 is less than the voltage needed to achieve the desired ventilation (e.g., a desired pressure or flow volume). As discussed below, example situations in which controller 28 may activate voltage adjuster 30 may include, e.g., fast ramp-up operations, high speed operation, high altitude operation, ventilation of a large adult, and/or where the voltage supplied by the active power source (e.g., a battery) has diminished.

Controller 28 may deactivate voltage adjuster 30 if the voltage supplied by the currently-active power source 14 is appropriate (e.g., sufficient) for achieving the desired ventilation. Activating and deactivating voltage adjuster 30 at appropriate times may conserve power as compared to a continuously-active voltage adjuster 30.

Motor controller 28 may control blower motor 18 based on various input data, including, e.g., target ventilation parameters 206 received from patient settings interface 26, motor data 210, performance data 212, power source data 214 and/or environmental data 216. Motor controller 28 may include a calculation engine 218 configured to calculate an appropriate or required motor speed and/or acceleration based on such input data, and control the voltage provided to blower motor 18, including controlling voltage adjuster 30 to adjust the supplied voltage when appropriate. Calculation engine 218 may include or have access to any suitable software, algorithms, or other logic suitable for performing such calculations.

As discussed above, target ventilation parameters 206 may include any data received from patient settings interface 26. Motor data 210 may include various data regarding the particular blower motor 18 in the ventilator 12, e.g., data regarding motor speed (RPMs) vs. supply voltage. Motor data 210 may thus be particular to the particular motor 18 supplied in ventilator 12. In some embodiments, motor data 210 may be determined by testing the motor 18 (e.g., at the manufacturer) and stored in any suitable manner in ventilator 12, e.g., in a calibration EEPROM or using one or more resistors. Motor controller 28 may use such motor data 210, e.g., for determining the voltage that should be supplied to motor 18 to achieve a particular pressure or flow volume.

Power source data 214 may include data regarding the condition of one or more power sources 14 of ventilator 12. For example, such data may include the voltage and/or current provided by each power source 14, which may be monitored in any suitable manner, e.g., continuously or periodically, and communicated to motor controller 28. Motor controller 28 may use such data 214, e.g., in determining whether to activate voltage adjuster 30 to adjust (e.g., boost or decrease) the voltage provided to motor 18. For example, in an embodiment in which a battery is currently providing power to motor 18, the voltage supplied by the battery may diminish over time. The diminishing voltage may be monitored over time and communicated to motor controller 28 as power source data 214, and motor controller 28 may use such data 214 to control voltage adjuster 30.

Environmental data 216 may include data regarding the environment in which ventilator 12 is operating, e.g., the barometric pressure and/or altitude of ventilator 12. In some embodiments, ventilator 12 may include a barometer to monitor barometric pressure, which may be communicated to motor controller 28 as environmental data 216. Motor controller 28 may use such data 216, e.g., in determining whether to activate voltage adjuster 30 to adjust (e.g., boost or decrease) the voltage provided to motor 18.

Performance data 212 may include data relating various parameters and/or input data. For example, performance data 212 may include data particular to ventilator 12 or the ventilation system that includes ventilator 12, e.g., motor speeds (RPM) required for producing various air pressures or flow volumes. In some embodiments, performance data 212 may include data defining different performance levels (e.g., low performance and high performance).

Different performance levels (e.g., "high performance" and "low performance") may be defined based on the voltage(s) supplied by power source(s) 14 of ventilator 14. For instance, "high performance" operation of motor 18 may be defined as operation of motor 18 that requires greater voltage than (a) the maximum voltage currently supplied by the active power source 14, or (b) the minimum voltage that the active power source 14 can supply over time. Thus, the threshold(s) for distinguishing between different performance levels may be either static or dynamic, depending on the embodiment. The first standard [standard (a)] may be used, e.g., in a system in which the voltage currently supplied by the active power source 14 is monitored and fed back to motor controller 28 as input such that motor controller 28 may adjust its calculations dynamically. To illustrate the difference between the two example standards, suppose ventilator 12 runs off of a battery that provides 24V when new or fully charged, but diminishes to 20V over time. Further suppose that the battery currently provides 22V. Under the first standard [standard (a)], "high performance" operation of motor 18 may be defined as any operation requiring more than the voltage currently supplied by the battery—i.e., 22V. Under the second standard [standard (b)], "high performance" operation of motor 18 may be defined as any operation requiring more than the minimum voltage supplied by the battery—i.e., 20V.

To determine whether motor 18 requires more voltage than provided by the active power source 14, motor controller 28 may determine the voltage required by motor 18 for the desired operation based on various factors. For example, the voltage required by motor 18 may be determined based on the desired motor speed and/or motor acceleration (increase in motor speed within x time period). As another example, the voltage required by motor 18 may be determined based on various factors related to motor speed and/or motor acceleration, e.g., the desired pressure, the desired flow volume, and/or the altitude.

For example, where the performance level is defined based on the minimum voltage that the active power source 14 will supply over time [standard (b)], static thresholds for distinguishing between different performance levels (e.g., "high performance" and "low performance") may be defined based on known minimum voltages of the relevant power source(s) 14. For instance, if ventilator 12 runs off of a power source 14 that fluctuates between 25V and 30V, static thresholds for distinguishing between "high performance" and "low performance" may be defined based on the 25V value.

In other embodiments, different performance levels may be defined based on various operational circumstances. For example, "high performance" motor operation may be defined as motor operation under any of the following circumstances: (a) fast ramp up, (b) high speed operation, and (c) high altitude operation; "low performance" motor operation may be defined as motor operation under any other circumstance. Each "high performance" factor may have corresponding thresholds for distinguishing between "high performance" and "low performance." Again, such thresholds for distinguishing between different performance levels may be static or dynamic.

In addition, voltage adjuster 30 may be operable to adjust the voltage provided to blower motor 18 as appropriate. For example, voltage adjuster 30 may "boost," or increase, the voltage provided to blower motor 18, e.g., when the voltage supplied to motor 18 by the active power source 14 is less than the voltage needed to achieve the desired ventilation (e.g., a desired pressure or flow volume). As discussed above, voltage adjuster 30 may be controlled by motor controller 28. Voltage adjuster 30 may include any suitable circuitry for boosting voltage. For example, voltage adjuster 30 may include a standard circuitry DC-DC voltage converter. In one particular embodiment, voltage adjuster 30 includes a DC-DC voltage converter capable of delivering 100 watts of power.

In some embodiments, voltage adjuster 30 may provide a voltage boost according to a binary on/off protocol, either providing a predetermined voltage boost or not providing a voltage boost. For example, voltage adjuster 30 may be configured to boost the voltage to a predetermined level (e.g., 26V) regardless of the input voltage. As another example, power adjust system 30 may be configured to boost the voltage by a particular amount (e.g., by 5V). Similarly, in some embodiments, voltage adjuster 30 may provide a voltage reduction according to a binary on/off protocol, either providing a predetermined voltage reduction or not providing a voltage reduction.

In other embodiments, voltage adjuster 30 may be configured to provide various levels of voltage boost or voltage reduction as desired. For example, voltage adjuster 30 may be configured to boost or reduce the voltage to one of a number of predetermined levels (e.g., to 26V, 28V, or 30V) based on a determination of the voltage required for the motor operation. As another example, voltage adjuster 30 may be configured to boost or reduce the voltage by one of a number of predetermined amounts (e.g., by 2V, 4V, or 6V) based on a determination of the voltage required for the motor operation and/or the voltage currently supplied by the active power source. As yet another example, voltage adjuster 30 may be configured to boost or reduce the voltage by an amount that dynamically changes over time (e.g., in an analog or digital manner) based on various input data, e.g., target ventilation parameters 206 received from patient settings interface 26, motor data 210, performance data 212, power source data 214 and/or environmental data 216. For example, as the voltage provided by a battery diminishes over time, voltage adjuster 30 may incrementally increase an amount of voltage boost accordingly over time.

Figure 5:
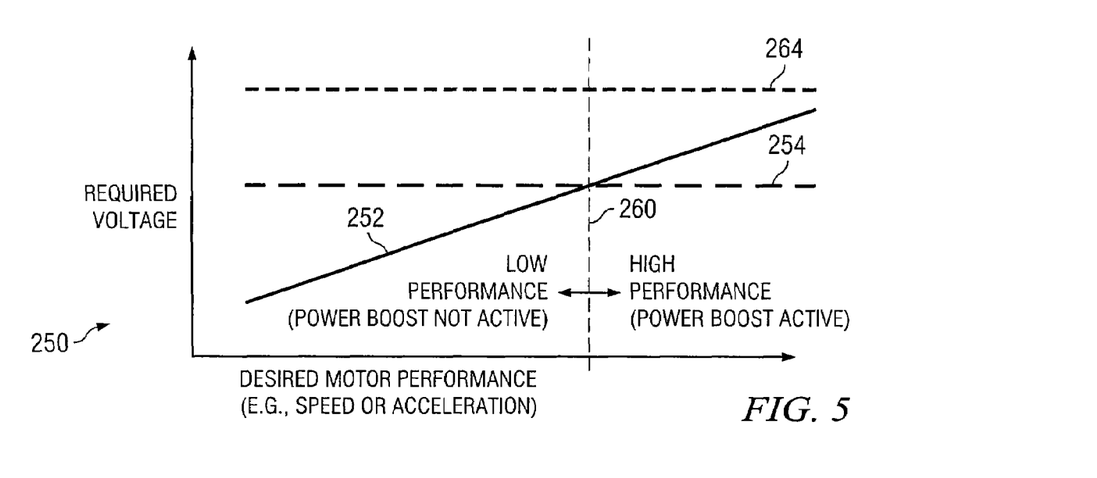
FIG. 5 is a graph illustrating example motor data, an indication of the interrelation between motor data, performance data, and/or power source data, and a distinction between "high performance" and "low performance" operation of a blower motor, according to one embodiment.

FIG. 5 is a graph 250 illustrating example motor data 210, an indication of the interrelation between motor data 210, performance data 212, and/or power source data 214, and the distinction between "high performance" and "low performance" operation of blower motor 18, according to an example embodiment. Graph 250 includes a line 252 representing an example relationship between the required voltage supplied to motor 18 (y-axis) vs. desired motor performance (e.g., motor speed or acceleration) for the particular blower motor 18. Thus, line 252 may indicate the voltage required to achieve various levels of motor performance for a particular blower motor 18. Although indicated in FIG. 5 as a linear relationship (i.e., a straight line on graph 250), such relationship may be non-linear in any manner. The relationship indicated by line 252 may be determined by testing the particular motor 18 and/or may be stored in ventilator 12 as motor data 210, e.g., as discussed above.

The voltage supplied by the active power source 14 is indicated in graph 250 by horizontal line 254. In some embodiments (e.g., embodiments in which the voltage supplied by power source 14 is continuously or periodically monitored), line 254 may represent the voltage currently supplied by the active power source 14. In other embodiments, line 254 may represent the minimum voltage that may be supplied by the active power source 14 over time. For example, if a battery is known to provide voltage in the range of 20V-24V over the life of the battery, line 254 may represent 20V.

Because line 252 represents required voltage vs. desired motor performance for motor 18, and line 254 indicates the voltage supplied by the active power source 14, the intersection of lines 252 and 254 may indicate a threshold—indicated by line 260—at which a voltage boost may be appropriate or necessary. In other words, in order to provide a motor speed or acceleration to the right of line 260, motor controller 28 may activate voltage adjuster 30 to boost the supply voltage as appropriate. In some embodiments, line 260 may define the distinction between "high performance" and "low performance" operation of motor 18, with "low performance" operation being defined to the left of line 260, and "high performance" operation being defined to the right of line 260.

Graph 250 also illustrates a line 264 indicating an example boosted voltage level provided by activating voltage adjuster 30 according to one embodiment. In this embodiment, the boosted voltage level is greater than or equal to the maximum voltage required for providing the maximum level of performance. In some embodiments, the boosted voltage level may be a predetermined voltage determined based on test data regarding a number of blower motors, e.g., such that the boosted voltage level is greater than or equal to the maximum voltage required for providing the maximum level of performance for any of the tested motors (e.g., the least efficient tested motor). In other embodiments, as discussed above, the amount of voltage boost may be dynamic and/or may depend on the currently supplied voltage. For example, in some embodiments, voltage adjuster 30 may boost the supplied voltage by an amount just sufficient to achieve the voltage required to provide the currently desired performance.

Figure 6:
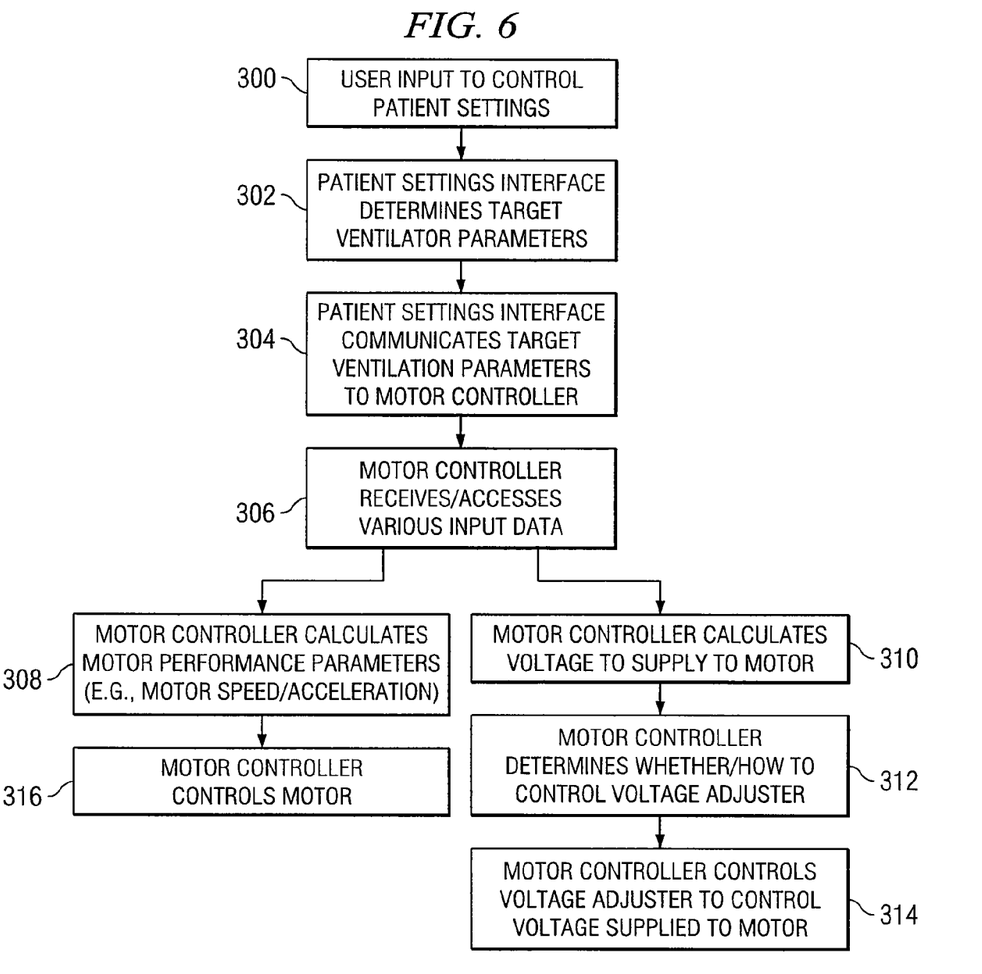
FIG. 6 illustrates an example method for controlling operation of a blower motor using a voltage adjuster, according to one embodiment.

FIG. 6 illustrates an example method for controlling the operation of a blower motor 18 using a voltage adjuster 30, according to one embodiment. At step 300, a user (e.g., a caregiver) may enter input 202 to ventilator 26, e.g., via patient settings interface 26. For example, the user may access, set, modify, or otherwise control one or more patient settings 204, e.g., one or more patient or environmental parameters and/or breath delivery parameters.

At step 302, patient settings interface 26 may determine one or more ventilator parameters 206 based on user input 202. For example, patient settings interface 26 may determine a target pressure or flow volume based at least on user input 202. As another example, patient settings interface 26 may determine a motor speed or motor acceleration for providing a particular target pressure or flow volume defined by patient settings 204. At step 304, patient settings interface 26 may communicate the one or more target ventilation parameters 206 to motor controller 28.

At step 306, motor controller 28 may receive and/or access various input data, e.g., target ventilation parameters 206, motor data 210, performance data 212, power source data 214 and/or environmental data 216. Such data may be useful for calculating or determining (a) how to control blower motor 18 and/or (b) how to control voltage adjuster 30 for regulating the voltage supplied to blower motor 18.

At step 308, motor controller 28 may calculate or determine one or more motor performance parameters (e.g., motor speed and/or acceleration) based on the various input data received at step 306. In some instances, motor controller 28 may calculate or determine one or more motor performance parameters required or appropriate for achieving the target ventilation parameters 206 received from patient settings interface 26. For example, motor controller 28 may calculate a motor speed suitable for generating a particular air pressure (target ventilation parameter 206)

based on performance data 210 defining a motor speed vs. pressure relationship for the particular ventilation system and/or motor data 210 regarding the particular blower motor 18.

At step 310, motor controller 28 may calculate or determine a voltage required or appropriate for achieving (a) the one or more motor performance parameters determined at step 308, based on the various input data received at step 306 and/or (b) the target ventilation parameters 206 received from patient settings interface 26. For example, motor controller 28 may calculate a voltage required for providing a particular motor speed (motor performance parameter) based on motor data 210 defining a motor speed vs. applied voltage relationship for the particular blower motor 18. As another example, motor controller 28 may calculate a voltage required for providing a particular air pressure (target ventilation parameter 206) based on performance data 210 defining a motor speed vs. pressure relationship for the particular ventilation system and motor data 210 defining a motor speed vs. applied voltage relationship for the particular blower motor 18.

At step 312, motor controller 28 may determine whether to activate and/or how to control voltage adjuster 30 such that motor 18 is supplied with sufficient voltage to achieve the motor performance parameter(s) determined at step 308. Such determination may be based at least on the required voltage determined at step 310 and power source data 214, which may indicate the voltage (e.g., the current voltage and/or the minimum voltage) supplied by the active power source 14. As discussed above, in some embodiments, motor controller 28 may compare the required voltage determined at step 310 with the voltage (e.g., the current voltage and/or the minimum voltage) supplied by the active power source 14. If the supplied voltage is less than the required voltage, motor controller 28 may determine to activate (or keep active) voltage adjuster 30 to provide a voltage boost. In some embodiments, motor controller 28 may also determine a level or magnitude of voltage boost to be provided by voltage adjuster 30. However, if the supplied voltage is greater than or equal to the required voltage, motor controller 28 may determine to deactivate (or keep inactive) voltage adjuster 30.

In other embodiments or situations, motor controller 28 may determine whether to activate voltage adjuster 30 to decrease the voltage supplied to motor 18, based at least on the required voltage determined at step 310 and power source data 214, which may indicate the voltage (e.g., the current voltage and/or the minimum voltage) supplied by the active power source 14. For example, motor controller 28 may compare the required voltage determined at step 310 with the voltage (e.g., the current voltage and/or the minimum voltage) supplied by the active power source 14. If the supplied voltage is greater than the required voltage by a threshold (which may be predetermined or determined dynamically), motor controller 28 may determine to activate voltage adjuster 30 to decrease the voltage supplied to motor 18. In some embodiments, motor controller 28 may also determine a level or magnitude of voltage reduction to be provided by voltage adjuster 30.

At step 314, motor controller 28 may control voltage adjuster 30 as determined at step 312 to control the voltage supplied to motor 18. For example, motor controller 28 may send signals to activate voltage adjuster 30, deactivate voltage adjuster 30, or (in some embodiments) adjust the level or magnitude of voltage boost provided by voltage adjuster 30.

At step 316, motor controller 28 may control blower motor 18 based on the motor performance parameter(s) determined at step 308. For example, motor controller 28 may control blower motor 18 to operate at a particular speed or to ramp up to a particular speed with a particular acceleration.

In various embodiments, the steps of the method discussed above may be performed in any suitable order, and any two or more steps may be performed fully or partially simultaneously. In addition, in some embodiments, the method described above may include one or more additional steps and/or may exclude one or more of the steps described above.

In addition, although this document focuses on systems and methods for boosting the supplied voltage as appropriate, similar systems and/or methods may be provided for decreasing the supplied voltage as appropriate. For example, voltage adjuster 30 may be operable to decrease voltage supplied to motor 18 using some or all of the systems and/or methods discussed above for boosting such voltage.

Although the disclosed embodiments have been described in detail, it should be understood that various changes, substitutions and alterations can be made to the embodiments without departing from their spirit and scope.

What is claimed is:

1. A method for controlling a motor for use in a ventilation system, comprising:
   receiving one or more target ventilation parameters regarding the ventilation of a patient;
   based at least on the one or more received target ventilation parameters, calculating one or more motor performance parameters for achieving the one or more target ventilation parameters;
   based at least on the one or more calculated motor performance parameters, performing a voltage adjustment analysis for controlling a voltage adjustment system configured to adjust a voltage applied to the motor;
   activating the voltage adjustment system based on a first result of the voltage adjustment analysis;
   not activating the voltage adjustment system based on a second result of the voltage adjustment analysis; and
   controlling the motor based on the one or more calculated motor performance parameters.

2. A method according to claim 1, wherein activating the voltage adjustment system comprises activating the voltage adjustment system to increase a voltage applied to the motor.

3. A method according to claim 1, wherein activating the voltage adjustment system comprises activating the voltage adjustment system to decrease a voltage applied to the motor.

4. A method according to claim 1, wherein the voltage adjustment analysis includes:
   determining a first voltage for achieving the one or more calculated motor performance parameters;
   accessing power supply data regarding a second voltage supplied by a power supply; and
   comparing the first voltage and the second voltage.

5. A method according to claim 4, wherein
   activating the voltage adjustment system based on a first result of the voltage adjustment analysis comprises activating the voltage adjustment system if the second voltage is less than the first voltage; and
   not activating the voltage adjustment system based on a first result of the voltage adjustment analysis comprises not activating the voltage adjustment system if the second voltage is greater than the first voltage.

6. A method according to claim 4, wherein activating the voltage adjustment system based on a first result of the voltage adjustment analysis comprises activating the voltage adjustment system if the second voltage is greater than the first voltage by a predetermined threshold.

7. A method according to claim 1, wherein the voltage adjustment analysis comprises determining a voltage to apply to the motor to achieve the one or more motor performance parameters.

8. A method according to claim 1, further comprising receiving motor data regarding the motor; and
wherein the voltage adjustment analysis is based at least on the one or more calculated motor performance parameters and the received motor data.

9. A method according to claim 1, further comprising accessing motor data regarding the motor; and
wherein the one or more motor performance parameters are calculated based at least on the motor data and the one or more target ventilation parameters.

10. A method according to claim 9, wherein the motor data defines a relationship between voltage supplied to the motor and one or more performance parameters of the motor.

11. A method according to claim 10, wherein the motor data defines a relationship between voltage supplied to the motor and a speed of the motor.

12. A method according to claim 9, wherein the motor data is determined based on physical testing of the motor.

13. A method according to claim 1, wherein the one or more motor performance parameters comprise at least one of a motor speed and a motor acceleration.

14. A method according to claim 1, further comprising adjusting a magnitude of voltage increase provided by the voltage adjustment system based on a third result of the voltage adjustment analysis.

15. A method according to claim 1, wherein the one or more target ventilation parameters comprise at least one of a target air pressure and a target air flow volume.

16. A method according to claim 1, wherein the voltage adjustment system comprises a DC-DC voltage converter.

17. A method according to claim 1, further comprising:
periodically repeating the voltage adjustment analysis; and
controlling the voltage adjustment system based on the result of each voltage adjustment analysis.

18. A method for controlling a motor for use in a ventilation system, comprising:
receiving one or more target ventilation parameters regarding the ventilation of a patient;
based at least on the one or more received target ventilation parameters, performing a voltage adjustment analysis for controlling a voltage adjustment system, the voltage adjustment system configured to adjust a voltage applied to the motor;
activating the voltage adjustment system based on a first result of the voltage adjustment analysis;
not activating the voltage adjustment system based on a second result of the voltage adjustment analysis; and
controlling the motor based on the one or more calculated motor performance parameters.

19. A method for controlling a motor for use in a ventilation system, comprising:
receiving one or more parameters regarding the ventilation of a patient;
identifying from a plurality of motor performance levels a particular motor performance level corresponding to the one or more received parameters; and
controlling a voltage adjustment system based on the identified motor performance level, including:
activating the voltage adjustment system if the identified motor performance level is a first performance level, wherein activating the voltage adjustment system adjusts a voltage applied to the motor; and
not activating the voltage adjustment system if the identified motor performance level is a second performance level.

20. A method according to claim 19, wherein activating the voltage adjustment system increases a voltage applied to the motor.

21. A method according to claim 19, wherein activating the voltage adjustment system decreases a voltage applied to the motor.

22. A method according to claim 19, further comprising:
calculating one or more motor performance parameters for achieving the one or more received parameters; and
controlling the motor based on the one or more calculated motor performance parameters.

23. A method according to claim 19, wherein the first performance level is a high performance level and the second performance level is a low performance level.

24. A method according to claim 19, wherein the one or more parameters corresponding to the first performance level include at least one of altitude and patient size.

25. A system for controlling a motor for use in a ventilation system, comprising:
a motor;
a voltage adjustment system operable to adjust a voltage applied to the motor;
a user interface configured to receive patient settings input from a user and to communicate one or more target ventilation parameters; and
a motor controller configured to receive the one or more target ventilation parameters from the user interface;
the motor controller including a calculation engine configured to:
calculate one or more motor performance parameters for achieving the one or more target ventilation parameters; and
based at least on the one or more calculated motor performance parameters, perform a voltage adjustment analysis for controlling the voltage adjustment system; and
the motor controller further including a voltage adjuster controller configured to activate the voltage adjustment system based on a first result of the voltage adjustment analysis and to not activate the voltage adjustment system based on a second result of the voltage adjustment analysis.

26. A system according to claim 25, wherein the motor controller is configured to control the motor based on the one or more calculated motor performance parameters.

27. A system according to claim 25, wherein the voltage adjustment system operable to increase a voltage applied to the motor.

28. A system according to claim 25, wherein the voltage adjustment system operable to increase or decrease a voltage applied to the motor.

29. A system for controlling a motor for use in a ventilation system, comprising:
motor means;
voltage adjusting means for adjusting a voltage applied to the motor means;

interface means for receiving patient settings input from a user and for communicating one or more target ventilation parameters; and motor controlling means for:
- receiving the one or more target ventilation parameters from the interface means;
- calculating one or more motor performance parameters for achieving the one or more target ventilation parameters; and
- based at least on the one or more calculated motor performance parameters, performing a voltage adjustment analysis for controlling the voltage adjustment system; and voltage adjustment controlling means for activating the voltage adjusting means based on a first result of the voltage adjustment analysis and to not activate the voltage adjusting means based on a second result of the voltage adjustment analysis.

30. A computer-readable medium including computer-executable instructions for controlling a motor for use in a ventilation system, the computer-executable instructions comprising:

instructions for receiving one or more target ventilation parameters regarding the ventilation of a patient;

instructions for calculating one or more motor performance parameters for achieving the one or more target ventilation parameters;

instructions for performing a voltage adjustment analysis for controlling a voltage adjustment system configured to adjust a voltage applied to the motor, the voltage adjustment analysis based at least on the one or more calculated motor performance parameters;

instructions for activating the voltage adjustment system based on a first result of the voltage adjustment analysis;

instructions for not activating the voltage adjustment system based on a second result of the voltage adjustment analysis; and instructions for controlling the motor based on the one or more calculated motor performance parameters.

* * * * *

UNITED STATES PATENT AND TRADEMARK OFFICE
CERTIFICATE OF CORRECTION

| | | |
|---|---|---|
| PATENT NO. | : 7,369,757 B2 | Page 1 of 1 |
| APPLICATION NO. | : 11/420167 | |
| DATED | : May 6, 2008 | |
| INVENTOR(S) | : John M. Farbarik | |

It is certified that error appears in the above-identified patent and that said Letters Patent is hereby corrected as shown below:

On the title page, item [56], under U.S. Patent Documents, insert:

--3,599,639   08/1971   Spotz et al. ............ 128/276
4,301,793   11/1981   Thompson .............. 128/204.21
7,244,106   07/2007   Kallman et al. ......... 417/44.1
2004/010412 A1   07/2007   Kallman et al. ......... 417/44.1--

On the title page, item [56], under Foreign Patent Documents, insert:

--EP 0518538   A2   12/1992
JP 57-110100   A    07/1982--

Signed and Sealed this

Twelfth Day of May, 2009

JOHN DOLL
*Acting Director of the United States Patent and Trademark Office*